(12) United States Patent
Henry

(10) Patent No.: US 10,814,050 B2
(45) Date of Patent: Oct. 27, 2020

(54) DENTAL SURGICAL SUCTION APPARATUS

(71) Applicant: Rolin S. Henry, Bowie, MD (US)

(72) Inventor: Rolin S. Henry, Bowie, MD (US)

( * ) Notice: Subject to any disclaimer, the term of this patent is extended or adjusted under 35 U.S.C. 154(b) by 0 days.

(21) Appl. No.: 14/776,869

(22) PCT Filed: Mar. 15, 2014

(86) PCT No.: PCT/IB2014/059861
§ 371 (c)(1),
(2) Date: Sep. 15, 2015

(87) PCT Pub. No.: WO2014/141215
PCT Pub. Date: Sep. 18, 2014

(65) Prior Publication Data
US 2016/0038661 A1   Feb. 11, 2016

Related U.S. Application Data

(60) Provisional application No. 61/789,772, filed on Mar. 15, 2013.

(51) Int. Cl.
*A61M 1/00* (2006.01)
*A61C 17/08* (2006.01)

(52) U.S. Cl.
CPC ........... *A61M 1/0086* (2014.02); *A61C 17/08* (2019.05); *A61M 1/008* (2013.01); *A61M 1/0039* (2013.01); *A61M 2207/00* (2013.01)

(58) Field of Classification Search
CPC ..... A61C 17/04; A61C 17/043; A61C 19/007; A61M 1/0003; A61M 1/0039
USPC ............. 433/91, 95, 96; 600/156; 606/15
See application file for complete search history.

(56) References Cited

U.S. PATENT DOCUMENTS

| | | | |
|---|---|---|---|
| 4,083,115 A | 4/1978 | McKelvey | |
| 4,487,600 A * | 12/1984 | Brownlie | A61M 1/008 433/95 |
| 4,878,900 A * | 11/1989 | Sundt | A61M 1/0039 285/921 |
| 5,013,300 A * | 5/1991 | Williams | A61M 1/008 433/91 |

(Continued)

FOREIGN PATENT DOCUMENTS

WO    9320776 A1    10/1993

*Primary Examiner* — Nicholas D Lucchesi
(74) *Attorney, Agent, or Firm* — Alfred F. Hoyte, Jr.; Michael Razavi

(57) ABSTRACT

A dental surgical suction apparatus combines the features and benefits of a surgical suction tip and a saliva ejector. The apparatus creates a more powerful suction force than provided by a saliva ejector by itself and can allow for better suctioning during oral surgery procedures and sedation, where keeping saliva and blood secretion from the throat can be critical, while also providing a device that is less traumatic to a patient's mouth. The apparatus can include a rigid tubular handle portion configured to releasably attach to a receiving port configured to receive a surgical suction tip on one end, a flexible tube portion connected to another end of the rigid tubular handle portion, and a soft tip portion connected to another end of the flexible tube portion. The soft tip portion includes a plurality of openings configured to minimize complete obstruction during suctioning.

9 Claims, 5 Drawing Sheets

(56) References Cited

U.S. PATENT DOCUMENTS

| | | | | |
|---|---|---|---|---|
| 5,441,410 | A * | 8/1995 | Segerdal | A61C 17/043 433/93 |
| 5,464,397 | A * | 11/1995 | Powers, Jr. | A61M 1/0039 433/95 |
| 5,704,785 | A * | 1/1998 | Young | A61C 17/043 433/91 |
| 6,068,476 | A | 5/2000 | Point | |
| 6,129,547 | A * | 10/2000 | Cise | A61C 17/0208 433/80 |
| 6,159,226 | A | 12/2000 | Kim | |
| 6,183,254 | B1 * | 2/2001 | Cohen | A61C 17/043 433/92 |
| 6,280,190 | B1 * | 8/2001 | Hoffman | A61C 17/043 433/91 |
| 6,299,444 | B1 * | 10/2001 | Cohen | A61C 17/043 433/91 |
| 7,066,903 | B2 * | 6/2006 | Yarger | A61M 1/0086 604/118 |
| 7,335,023 | B2 * | 2/2008 | Mahlmann | A61C 17/08 433/96 |
| 7,625,207 | B2 * | 12/2009 | Hershey | A61C 1/16 433/100 |
| 7,744,371 | B1 * | 6/2010 | Griffin | A61C 17/043 285/181 |
| 7,938,794 | B2 * | 5/2011 | Rehman | A61M 1/008 604/19 |
| 8,545,401 | B2 * | 10/2013 | Hajarian | A61M 1/008 433/91 |
| 8,845,618 | B2 * | 9/2014 | Hensler | A61M 1/0086 604/101.01 |
| 9,283,308 | B2 * | 3/2016 | Hajarian | A61M 1/008 |
| 2001/0024778 | A1 | 9/2001 | Hoffman | |
| 2003/0054317 | A1 * | 3/2003 | Burney | A61C 17/043 433/96 |
| 2008/0145815 | A1 * | 6/2008 | Hershey | A61C 1/16 433/91 |

\* cited by examiner

DENTAL SURGICAL SUCTION APPARATUS

CROSS-REFERENCE TO RELATED APPLICATIONS

This application claims priority from U.S. Provisional Patent Application Ser. No. 61/789,772, filed Mar. 15, 2013, the disclosure of which is hereby incorporated by reference in its entirety.

STATEMENT REGARDING FEDERALLY SPONSORED RESEARCH OR DEVELOPMENT

Not Applicable.

BACKGROUND

Field

The disclosed subject matter is generally directed to devices that can be used during oral surgery, and more particularly, to a dental surgical suction apparatus.

Description of Related Art

It is a known dental practice to employ an evacuating device, commonly called a saliva ejector, for removing saliva and debris from the mouth of a patient during the performance of dental work, such as cleaning and filling teeth. An illustration of a known saliva ejector is shown in FIG. 1A. Another example can also be found in U.S. Pat. No. 3,777,756. Known dental saliva ejectors can include an ejector tube having an inlet end to receive the saliva and any debris entrained therein. The other end of a known ejector can be connected to a hose that is attached to a source of reduced pressure, such as a vacuum pump.

Known saliva ejectors, however, can be inefficient for providing sufficient suction, especially during oral surgery procedures and sedation, where keeping saliva and blood secretions from the throat can be critical. Often, when there is a lot of bleeding and thick saliva, known saliva ejectors can get clogged with blood or saliva, causing them to lose efficiency. In this situation, excessive saliva and blood could be allowed to go down a patient's throat. Flex-tube ejectors can be bendable and can hang in a patient's mouth, but they can often pull out of their holder on a suction tube.

FIG. 1B shows a known surgical suction tip. Another example can be found in U.S. Pat. No. 4,221,220. When it comes to suctioning the throat, known surgical suction tips can be too rigid and can easily cause trauma if not use cautiously. Such tips are also not as flexible when it comes to use in the vestibule, i.e., the part of the mouth outside the teeth. Also, rigidly-molded ejectors are not designed to hang in a patient's mouth.

Moreover, a dentist cannot simply stick a saliva ejector into the receiving suctioning port for a surgical suction tip. The saliva ejector tubing is typically one consistent diameter and the opening of a standard suctioning port for a surgical suction tip is much too large.

SUMMARY

In a dental surgical suction apparatus embodying the principles disclosed herein, a novel illustrative embodiment can include the features and benefits of a surgical suction tip with the features and benefits of a saliva ejector. The illustrative embodiments can have the effect of creating a more powerful suction force than provided by a saliva ejector by itself and can allow for better suctioning during oral surgery procedures and sedation, where keeping saliva and blood secretion from the throat can be critical, while also providing a device that is less traumatic to a patient's mouth.

One general aspect includes a dental surgical suction apparatus, including a rigid tubular handle portion configured on one end to releasably attach to a receiving port configured to receive a surgical suction tip on one end; a flexible tube portion connected to another end of the rigid tubular handle portion; and a soft tip portion connected to another end of the flexible tube portion, where the soft tip portion includes a plurality of openings configured to minimize complete obstruction during suctioning.

Implementations may include one or more of the following features. The dental surgical suction apparatus, where the receiving port is configured to be operatively connected to a vacuum source to provide for a suction through the dental surgical suction apparatus. The dental surgical suction apparatus where the rigid tubular handle portion and flexible tube portion are non-releasably attached. The dental surgical suction apparatus where the rigid tubular handle portion and flexible tube portion are releasably attached. The dental surgical suction apparatus where the flexible tube portion and soft tip portion are non-releasably attached. The dental surgical suction apparatus where the flexible tube portion and soft tip portion are releasably attached. The dental surgical suction apparatus where the inside diameter of the rigid tubular handle portion is greater than the inside diameter of the flexible tube portion.

One general aspect includes a method of making a dental surgical suction apparatus, including: providing a rigid tubular handle portion configured to releasably attach to a receiving port configured to receive a surgical suction tip on one end; connecting a flexible tube portion to another end of the rigid tubular handle portion; and connecting a soft tip portion to another end of the flexible tube portion, where the soft tip portion includes a plurality of openings configured to minimize complete obstruction during suctioning.

Implementations may include one or more of the following features. The method further including operatively connecting the receiving port to a vacuum source to provide for a suction through the dental surgical suction apparatus.

BRIEF DESCRIPTION OF THE DRAWINGS

As will be realized, different embodiments are possible, and the details disclosed herein are capable of modification in various respects, all without departing from the scope of the claims. Accordingly, the drawings and descriptions are to be regarded as illustrative in nature and not as restrictive. Like reference numerals or characters are used throughout the several views and embodiments to designate like components.

DETAILED DESCRIPTION

To facilitate an understanding of the principles upon which the subject matter disclosed herein is based, illustrative embodiments are described hereinafter with reference to their implementation as a dental surgical suction apparatus. It will be appreciated that the practical applications of these principles are not limited to this particular type of system. Rather, they can be equally employed in any other type of system that can provide for the efficient suctioning of various materials.

Figure 1A:
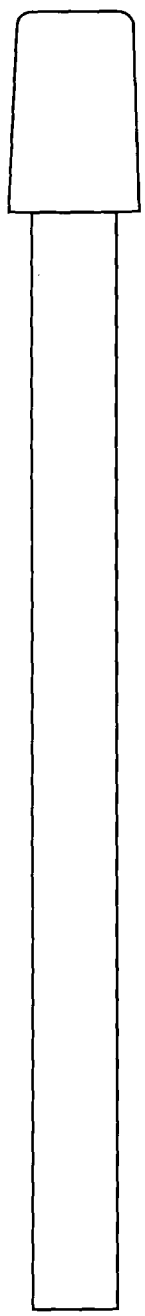
FIG. 1A shows a known saliva ejector.
Figure 1B:
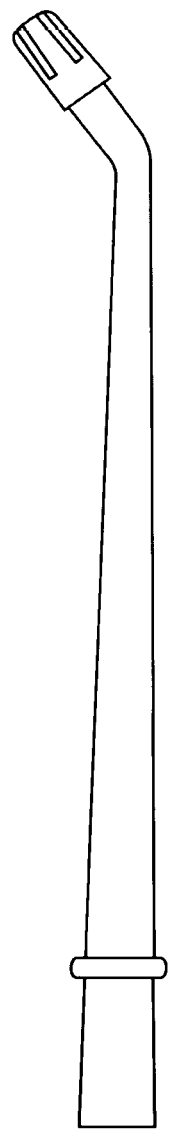
FIG. 1B shows a known surgical suction tip.
Figure 2:
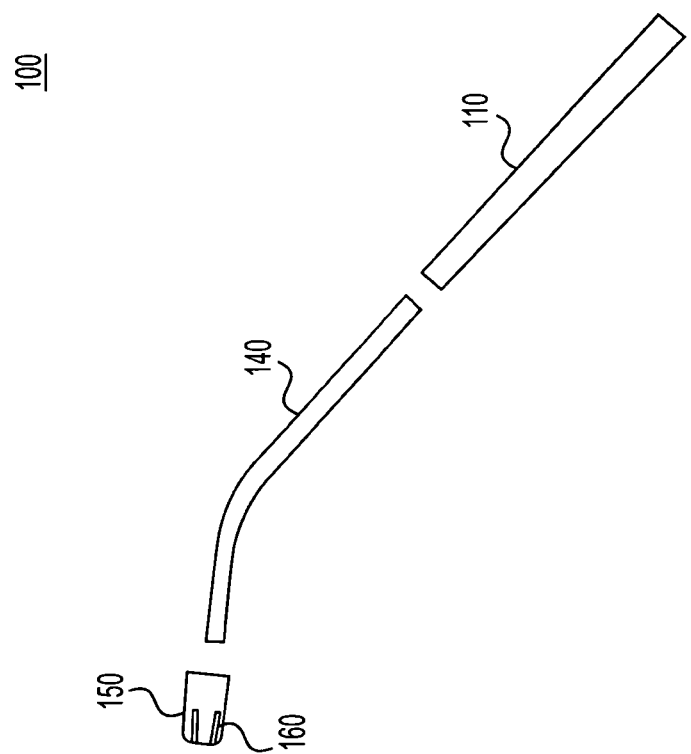
FIG. 2 shows an illustrative embodiment of a dental surgical suction apparatus.
Figure 2:
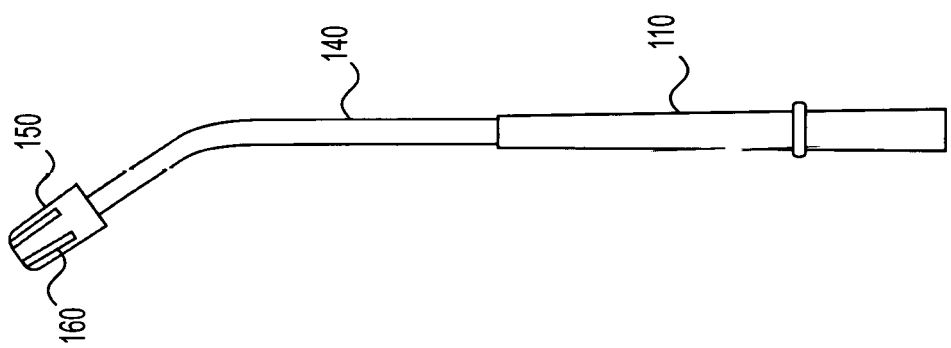
Figure 3:
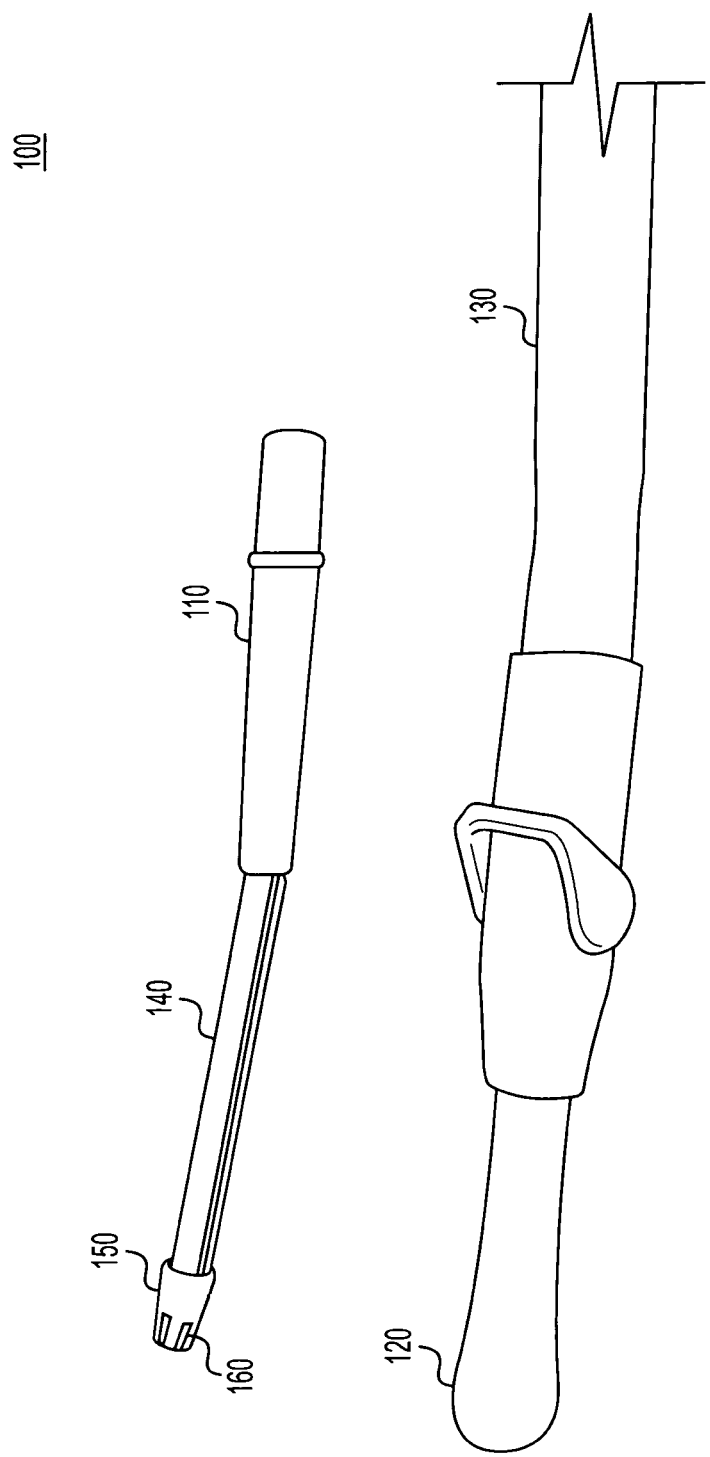
FIG. 3 shows an illustrative embodiment of a dental surgical suction apparatus next to a suctioning (e.g., receiving) port and tubing for a surgical suction tip.
Figure 4:
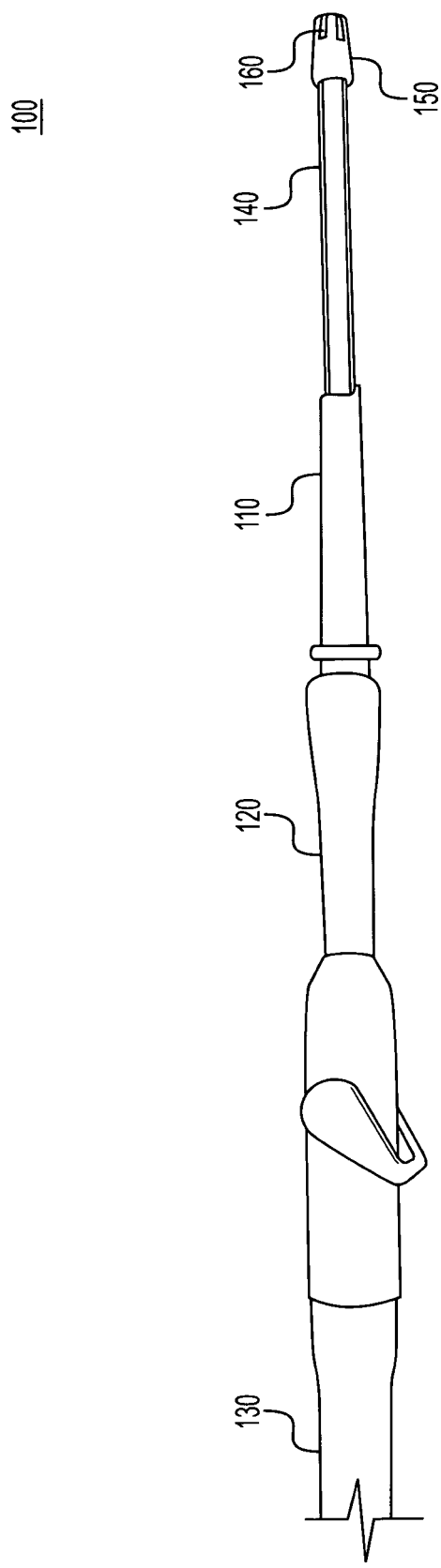
FIG. 4 shows an illustrative embodiment of a dental surgical suction apparatus connected to a suctioning port and tubing for a surgical suction tip.

FIGS. 2, 3 and 4 show illustrative embodiments of dental surgical suction apparatus 100. In an embodiment, dental surgical suction apparatus 100 can include rigid tubular handle portion 110. In an embodiment, rigid handle portion 110 can be configured to releasably attach at one end to a receiving port 120, which can also be referred to as a High Volume Evacuator (HVE), which may be configured to receive an industry-standard suction attachment-sized device, such as a surgical suction tip. Receiving port 120, or HVE, can be attached at another end via hose 130 to a vacuum source, such as a vacuum pump (not shown).

In an embodiment, rigid handle portion 110 can be made of a substantially rigid or inflexible material, such as plastic, metal, glass, rubber, or other suitable materials, to name a few non-limiting examples. In an embodiment, rigid handle portion 110 can be made of high-density polyethylene (HDPE) or PVC and manufactured by injection molding.

In an embodiment, flexible tube portion 140 can be made of a substantially flexible material, such as plastic, rubber, or other suitable materials and can be releasably or non-releasably attached to rigid handle portion 110. In an embodiment, flexible tube portion 140 can be wire-reinforced to easily form and maintain a desired shape. In an embodiment, flexible tube portion 140 can be made of flexible PVC and manufactured by an extrusion process.

In an embodiment, a tubular, for example, soft tip portion 150 can be releasably or non-releasably attached to flexible tube portion 140. In an embodiment, soft tip portion 150 can be attached to flexible tube portion by any suitable means, such as a friction fit, threaded connection, or a coupling, to name a few non-limiting examples.

In an embodiment, soft tip portion 150 can include a plurality of openings 160 that can help to minimize complete obstruction during suctioning, such as when a large particle or foreign body is encountered.

In an embodiment, soft tip portion 150 can be made of plastic, metal, glass, or rubber, for example, to name a few non-limiting examples. In an embodiment, soft tip portion can be made of soft materials to cushion upon contact. In an embodiment, soft tip portion 150 can be made of flexible PVC and manufactured by injection molding.

In an embodiment, the inside diameter of flexible tube portion 140 can be essentially constant. In an embodiment, the inside diameter of rigid handle portion 110 can be essentially constant or decreasing from where it attaches to receiving port 120 (e.g., greater diameter) to where it attaches to flexible tube portion 140 (e.g., smaller diameter). For example, the outside diameter of flexible tube portion 140 can be essentially the same size as the inside diameter of rigid handle portion 110 where they attach. In an embodiment, the outside diameter of rigid handle portion 110 can be sized to snugly fit into receiving port 120, thus providing a more powerful suctioning force of a surgical suctioning tip system with the benefits of a saliva ejector tip.

In an embodiment, several potential fitment solutions exist. For example, a press fit arrangement can be used where the parts, e.g., the rigid handle portion 110, the flexible tube portion 140, and soft tip portion 150 can be designed to have a snug friction fit. In some cases, the soft tip portion 150 may be too flexible to be rigidly retained onto the flexible tube portion 140 and may need to be bonded. In an embodiment, flexible tube portion 140 can be rigidly retained onto rigid handle portion 110.

In an embodiment, cohesive bonding using radio-frequency (RF) welding can be used to bond PVC parts. Ultrasonic welding and vibration welding can be used to bond olefinic parts. Adhesive bonding, e.g., solvent bonding, can be used with PVC parts and cyanoacrylate adhesive can be used for polyethylene parts, for example.

Various embodiments can have different materials and methods of fitment employed. For example, rigid handle portion 110 can be made of rigid PVC, flexible tube portion 140 can be made of flexible PVC and the soft tip portion 150 can be made of flexible PVC. The portions can be chemically bonded or joined using RF welding. In another non-limiting example, rigid handle portion 110 can be made of rigid HDPE, flexible tube portion 140 can be made of flexible PVC and soft tip portion 150 can be made of flexible PVC. Rigid handle portion 110 and flexible tube portion 140 can be chemically bonded whereas the soft tip portion 150 and flexible tube portion 140 can be chemically bonded. In another non-limiting example, rigid handle portion 110 can be made of HDPE, and flexible tube portion 140 and soft tip portion 150 can be made of thermoplastic olefin (TPO). Again, appropriate fitment techniques may be used.

In some cases the materials can be food-grade, rather than medical-grade plastics, for example. The materials chosen can be resistant to radiation to allow sterilization when packaged.

FIG. 3 shows an illustrative embodiment with dental surgical suction apparatus 100 next to receiving port 120, or HVE, which can be connected to hose 130. The other end of hose 130 can be attached to the previously mentioned vacuum source, such as a vacuum pump (not shown).

FIG. 4 shows an illustrative embodiment with dental surgical suction apparatus 100 connected to receiving port 120, or HVE, which can be connected to hose 130. The other end of hose 130 can be attached to the previously mentioned vacuum source, such as a vacuum pump (not shown).

The disclosed embodiments can provide a novel solution to problems that dentists face everyday in their practice. The disclosed embodiments can allow dentists to improve their efficiency without any significant changes in the way they currently perform their suctioning procedures.

The illustrative embodiments disclosed herein can provide desirable features found in a saliva ejector, such as a tip that allows the device to be gentle on the oral and gingival tissue, causing less trauma during suctioning. Additionally, the tip can have multiple openings that help to prevent complete obstruction during suctioning, such as when a large particle or foreign body is encountered. Moreover, a flexible portion can allow it to be bent in any direction and can be maintained in a bent position.

Similarly, the illustrative embodiments disclosed herein can provide desirable features found in a surgical suction tip, such as providing for more powerful and efficient suctioning of saliva and blood. Additionally, a portion of the dental surgical suction apparatus can be rigid, which can allow for more stability during use. A larger bore can also allow more saliva and blood to be removed during suctioning.

The above description is presented to enable a person skilled in the art to make and use the systems and methods described herein, and is provided in the context of a particular application and its requirements. Various modifications to the embodiments will be readily apparent to those skilled in the art, and the generic principles defined herein may be applied to other embodiments and applications without departing from the spirit and scope of the claims. Thus, there is no intention to be limited to the embodiments shown, but rather to be accorded the widest scope consistent with the principles and features disclosed herein.

What is claimed is:

1. A disposable dental surgical suction apparatus directly connectable to an HVE receiving port, the receiving port directly connected to an HVE vacuum source, the apparatus comprising:
   a rigid tubular handle portion having opposing ends and configured on one end to releasably attach directly to a the HVE receiving port;
   a flexible tube portion having opposing ends and connected to another end of the rigid tubular handle portion;
   a soft tip portion connected to another end of the flexible tube portion, the soft tip portion having a plurality of openings configured to minimize complete obstruction during suctioning;
whereby said single piece dental surgical suction apparatus is discarded after use said rigid tubular handle portion configured to be releasably coupled to said HVE receiving port;
   whereby said apparatus is disposed after each use.

2. The dental surgical suction apparatus of claim 1, wherein the rigid tubular handle portion and flexible tube portion are non-releasably attached.

3. The dental surgical suction apparatus of claim 1, wherein the rigid tubular handle portion and flexible tube portion are releasably attached.

4. The dental surgical suction apparatus of claim 1, wherein the flexible tube portion and soft tip portion are non-releasably attached.

5. The dental surgical suction apparatus of claim 1, wherein the flexible tube portion and soft tip portion are releasably attached.

6. The dental surgical suction apparatus of claim 1, wherein the inside diameter of the rigid tubular handle portion is greater than the inside diameter of the flexible tube portion.

7. A method of making a disposable dental surgical suction ejector, comprising; providing a rigid tubular handle portion configured to releasably attach directly to a HVE receiving port that is directly connected to an HVE vacuum source; connecting a flexible tube portion to another end of the rigid tubular handle portion; and connecting a soft tip portion to another end of the flexible tube portion, wherein the soft tip portion comprises a plurality of openings configured to minimize complete obstruction during suctioning.

8. A method of using a dental saliva ejector for an oral procedure, comprising; releasably attaching the dental saliva ejector to a HVE receiving port, which is connected to a source of HVE vacuum, wherein the dental saliva ejector comprises; a rigid tubular handle portion configured on one end to releasably attach to the HVE receiving port that is connected to the source of vacuum, a flexible tube portion connected to another end of the rigid tubular handle portion, and a soft tip portion connected to another end of the flexible tube portion, wherein the soft tip portion comprises a plurality of openings configured to minimize complete obstruction during suctioning; and disposing of said saliva ejector after use.

9. The apparatus of claim 1, wherein said rigid tubular handle portion includes a raised annular abutment member.

* * * * *